US012805732B2

(12) United States Patent
Lin et al.

(10) Patent No.: US 12,805,732 B2
(45) Date of Patent: Nov. 24, 2026

(54) SINGLE-ARM PHYSIOLOGICAL SIGNAL MEASURING SYSTEM

(71) Applicant: Ritum Biomedical Ltd., Taoyuan City (TW)

(72) Inventors: Wen-Chi Lin, Taoyuan City (TW); Yung-Hsin Chen, Taoyuan City (TW)

(73) Assignee: Ritum Biomedical Ltd., Taoyuan City (TW)

( * ) Notice: Subject to any disclaimer, the term of this patent is extended or adjusted under 35 U.S.C. 154(b) by 210 days.

(21) Appl. No.: 18/784,804

(22) Filed: Jul. 25, 2024

(65) Prior Publication Data

US 2025/0120599 A1 Apr. 17, 2025

(30) Foreign Application Priority Data

Oct. 16, 2023 (TW) ................................ 112139366

(51) Int. Cl.
*A61B 5/021* (2006.01)
*A61B 5/00* (2006.01)
(Continued)

(52) U.S. Cl.
CPC ...... *A61B 5/02125* (2013.01); *A61B 5/14552* (2013.01); *A61B 5/256* (2021.01);
(Continued)

(58) Field of Classification Search
CPC . A61B 5/02125; A61B 5/14552; A61B 5/256; A61B 5/282; A61B 5/6802;
(Continued)

(56) References Cited

U.S. PATENT DOCUMENTS 8,239,010 B2 8/2012 Banet et al.
8,328,728 B2 * 12/2012 Schecter ............ A61B 5/02116 600/509

(Continued)

FOREIGN PATENT DOCUMENTS

CN 1672631 A * 9/2005
DE 112021000615 T5 * 11/2022 ............ A61B 5/332

(Continued)

OTHER PUBLICATIONS

JP 2024109482 A English translation (Year: 2024).*

*Primary Examiner* — Jeffrey G. Hoekstra
(74) *Attorney, Agent, or Firm* — JCIPRNET

(57) ABSTRACT

A single-arm physiological signal measuring system, including a shell, a flexible electronic assembly, and an air bag, is provided. The flexible electronic assembly is disposed in the shell and surrounds to form a space. The flexible electronic assembly includes a photoplethysmography module, an electrocardiogram module, and a controller. The electrocardiogram module includes first and second electrocardiogram electrodes. The controller is electrically connected to the photoplethysmography module and the electrocardiogram module. The air bag is disposed between the shell and the flexible sensing assembly to push the flexible sensing assembly to change a size of the space. When the air bag is inflated, the photoplethysmography module, the first and second electrocardiogram electrodes are pushed by the air bag to touch an arm, so that the photoplethysmography module measures a blood oxygen saturation, the electrocardiogram module measures an electrocardiogram, and the controller calculates a blood pressure.

10 Claims, 7 Drawing Sheets

(51) Int. Cl.
*A61B 5/1455* (2006.01)
*A61B 5/256* (2021.01)
*A61B 5/282* (2021.01)

(52) U.S. Cl.
CPC ............ *A61B 5/282* (2021.01); *A61B 5/6802* (2013.01); *A61B 2560/0468* (2013.01); *A61B 2562/164* (2013.01); *A61B 2562/227* (2013.01)

(58) Field of Classification Search
CPC ...... A61B 2560/0468; A61B 2562/164; A61B 2562/227; A61B 5/02141; A61B 5/02225; A61B 5/02255; A61B 5/0245; A61B 5/02233; A61B 5/14551
See application file for complete search history.

(56) References Cited

U.S. PATENT DOCUMENTS

| | | | | |
|---|---|---|---|---|
| 10,420,476 | B2 * | 9/2019 | Moon | A61B 5/02125 |
| 11,020,057 | B2 * | 6/2021 | Baek | A61B 8/4281 |
| 2010/0298655 | A1 * | 11/2010 | McCombie | A61B 5/0205 600/301 |
| 2010/0298661 | A1 * | 11/2010 | McCombie | A61B 5/0205 600/587 |
| 2013/0109948 | A1 * | 5/2013 | Li | A61B 5/0095 600/407 |
| 2015/0164437 | A1 * | 6/2015 | McCombie | A61B 5/1117 600/301 |
| 2017/0079591 | A1 * | 3/2017 | Gruhlke | A61B 5/6898 |
| 2019/0298177 | A1 * | 10/2019 | Moon | A61B 5/0002 |
| 2019/0320912 | A1 * | 10/2019 | Chen | G16H 10/60 |
| 2022/0240793 | A1 * | 8/2022 | Chen | A61B 5/02007 |
| 2023/0200663 | A1 * | 6/2023 | McCombie | A61B 5/0024 600/595 |
| 2025/0120599 | A1 * | 4/2025 | Lin | A61B 5/6802 |

FOREIGN PATENT DOCUMENTS

| | | | | | |
|---|---|---|---|---|---|
| EP | 3669762 | A1 | * | 6/2020 | A61B 5/318 |
| EP | 3964124 | A1 | * | 3/2022 | A61B 5/02116 |
| JP | 2024109482 | A | * | 8/2024 | A61B 5/6831 |
| KR | 102486700 | B1 | * | 1/2023 | A61B 5/02108 |
| KR | 20230017966 | A | * | 2/2023 | A61B 5/321 |
| KR | 102854987 | B1 | * | 9/2025 | A61B 5/02416 |
| TW | I663956 | | | 7/2019 | |
| TW | 202237026 | | | 10/2022 | |
| TW | 202237026 | A | * | 10/2022 | A61B 5/02125 |
| TW | 1789139 | B | * | 1/2023 | A61B 5/6831 |
| TW | 202322750 | | | 6/2023 | |
| TW | M650590 | | | 1/2024 | |
| WO | WO-2016205414 | A1 | * | 12/2016 | G16H 30/40 |

* cited by examiner

SINGLE-ARM PHYSIOLOGICAL SIGNAL MEASURING SYSTEM

CROSS-REFERENCE TO RELATED APPLICATION

This application claims the priority benefit of Taiwan application serial no. 112139366, filed on Oct. 16, 2023. The entirety of the above-mentioned patent application is hereby incorporated by reference herein and made a part of this specification.

BACKGROUND

Technical Field

The disclosure relates to a measuring system, and in particular to a single-arm physiological signal measuring system.

Description of Related Art

The conventional manner of measuring blood pressure is to tie an air bag to the arm and inflate the air bag to compress the arm to obtain blood pressure information. Since such process causes discomfort to the user, the strap is released after a single measurement, so only short-term blood pressure information can be obtained.

SUMMARY

The disclosure provides a single-arm physiological signal measuring system, which can perform long-term physiological signal measurement using a single-arm measurement manner.

The disclosure provides a single-arm physiological signal measuring system, which includes a shell, a flexible electronic assembly, and an air bag. The flexible electronic assembly is disposed in the shell and surrounds to form a space. The flexible electronic assembly includes a photoplethysmography (PPG) module, an electrocardiogram (ECG) module, and a controller. The electrocardiogram module includes a first electrocardiogram electrode and a second electrocardiogram electrode. The controller is electrically connected to the photoplethysmography module and the electrocardiogram module. The air bag is disposed between the shell and the flexible electronic assembly to push the flexible electronic assembly to change a size of the space. An arm of a user is adapted to extend into the space. When the air bag is inflated, the photoplethysmography module, the first electrocardiogram electrode, and the second electrocardiogram electrode are pushed by the air bag to contact the arm, so that the photoplethysmography module measures a blood oxygen saturation of the user, the electrocardiogram module measures an electrocardiogram of the user, and the controller calculates a blood pressure of the user according to the blood oxygen saturation and the electrocardiogram.

In an embodiment of the disclosure, the flexible electronic assembly includes at least two hard circuit boards and at least one flexible circuit board or at least one flexible cable connecting the at least two hard circuit boards, the photoplethysmography module, the controller, the first electrocardiogram electrode, and the second electrocardiogram electrode are disposed on the at least two hard circuit boards, and the first electrocardiogram electrode and the second electrocardiogram electrode are disposed on two different ones of the at least two hard circuit boards.

In an embodiment of the disclosure, the single-arm physiological signal measuring system further includes a soft layer disposed on a surface of the flexible electronic assembly facing the space to cover the at least two hard circuit boards and the at least one flexible circuit board or the at least one flexible cable. The soft layer includes multiple openings. The openings expose the photoplethysmography module, the first electrocardiogram electrode, and the second electrocardiogram electrode.

In an embodiment of the disclosure, the flexible electronic assembly further includes a cell electrically connected to the controller, the photoplethysmography module, and the electrocardiogram.

In an embodiment of the disclosure, the air bag includes multiple pouches evenly arranged and communicated with each other. The flexible electronic assembly includes multiple hard circuit boards. The pouches correspond to the hard circuit boards.

In an embodiment of the disclosure, the air bag includes a pouch. The flexible electronic assembly includes multiple hard circuit boards. The pouch corresponds to the hard circuit boards.

In an embodiment of the disclosure, a projection of the air bag to the flexible electronic assembly covers the photoplethysmography module, the first electrocardiogram electrode, and the second electrocardiogram electrode.

In an embodiment of the disclosure, the shell includes an inflating port and a deflating port. The inflating port and the deflating port are communicated with the air bag. A one-way valve is disposed between the inflating port and the air bag.

In an embodiment of the disclosure, the single-arm physiological signal measuring system further includes an inflating system. The inflating system is detachably combined with the inflating port or the inflating system is fixed to the inflating port.

In an embodiment of the disclosure, the shell is in a C-shape or an O-shape.

Based on the above, in the single-arm physiological signal measuring system of the disclosure, the air bag is disposed between the shell and the flexible electronic assembly to push the flexible electronic assembly to change the size of the space. The arm of the user is adapted to extend into the space surrounded by the flexible electronic assembly. When the air bag is inflated, the photoplethysmography module, the first electrocardiogram electrode, and the second electrocardiogram electrode of the flexible electronic assembly are pushed by the air bag to contact the arm, so that the photoplethysmography module measures the blood oxygen saturation of the user, the electrocardiogram module of the flexible electronic assembly measures the electrocardiogram of the user, and the controller calculates the blood pressure of the user according to the blood oxygen saturation and the electrocardiogram. Compared with the conventional manner of measuring blood pressure by obtaining blood pressure information through strapping the air bag to the arm and inflating the air bag to compress the arm, which causes discomfort to the user and can only measure for a short period of time, the air bag of the single-arm physiological signal measuring system of the embodiment only needs to be inflated until the photoplethysmography module, the first electrocardiogram electrode, and the second electrocardiogram electrode contact the arm to obtain the blood oxygen saturation and the electrocardiogram, and the controller then calculates the blood pressure, which greatly improves the comfort of the user during the measurement process and can achieve long-term measurement.

DESCRIPTION OF THE EMBODIMENTS

Figure 1A:
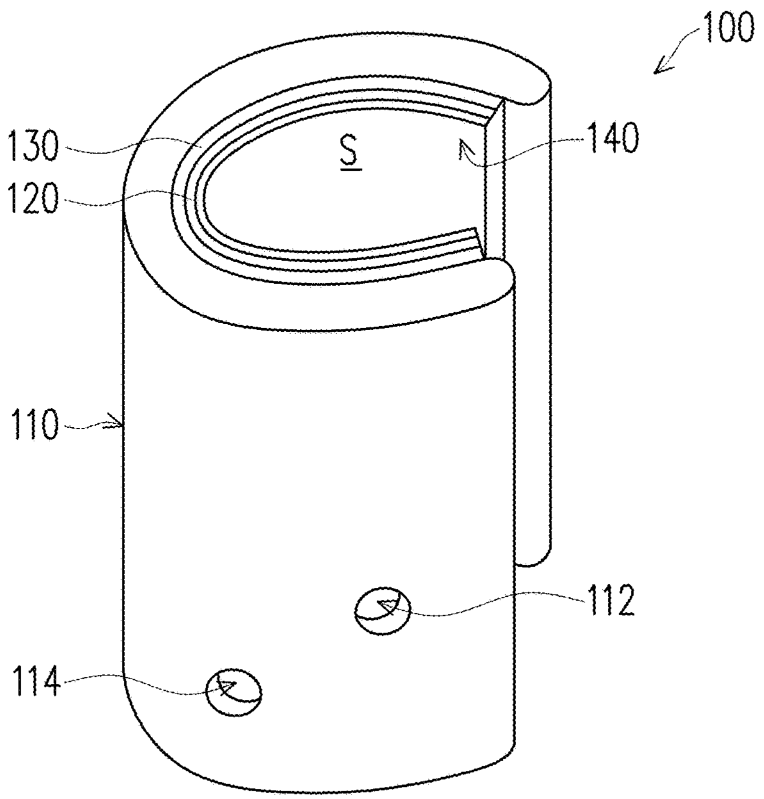
FIG. 1A is a schematic three-dimensional view of a single-arm physiological signal measuring system according to an embodiment of the disclosure.
Figure 1B:
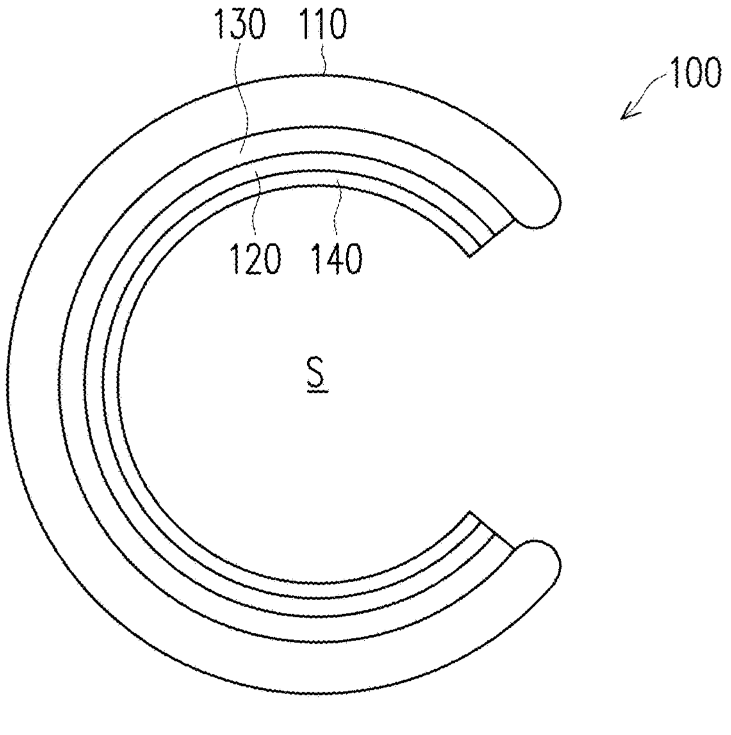
FIG. 1B is a schematic top perspective view of FIG. 1A.

FIG. 1A is a schematic three-dimensional view of a single-arm physiological signal measuring system according to an embodiment of the disclosure. FIG. 1B is a schematic top perspective view of FIG. 1A. It should be noted that in order to clearly show positions of a flexible electronic assembly 120 and an air bag 130, FIG. 1B presents the flexible electronic assembly 120 and the air bag 130 located inside in a perspective manner.

Please refer to FIG. 1A and FIG. 1B. A single-arm physiological signal measuring system 100 of the embodiment includes a shell 110, a flexible electronic assembly 120, and an air bag 130. In the embodiment, the shell 110 is in a C-shape. Of course, the shape of the shell 110 is not limited thereto. In other embodiments, the shell 110 may also be in an O-shape or other shapes.

As can be seen from FIG. 1A, the shell 110 includes an inflating port 112 and a deflating port 114. The inflating port 112 and the deflating port 114 are communicated with the air bag 130 (FIG. 1B). In addition, as shown in FIG. 1B, the flexible electronic assembly 120 is disposed in the shell 110 and surrounds to form a space S. The air bag 130 is disposed between the shell 110 and the flexible electronic assembly 120, and is configured to push the flexible electronic assembly 120 to change the size of the space S.

Figure 2A:
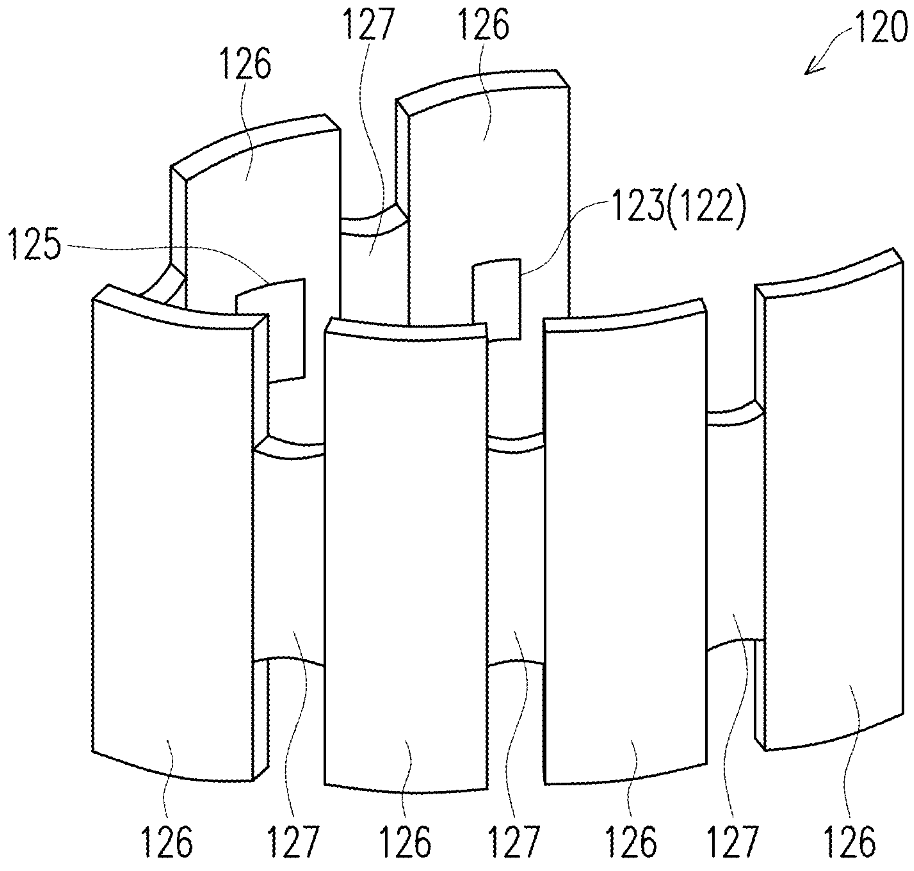
FIG. 2A is a schematic view of a flexible electronic assembly of the single-arm physiological signal measuring system of FIG. 1A.
Figure 2B:
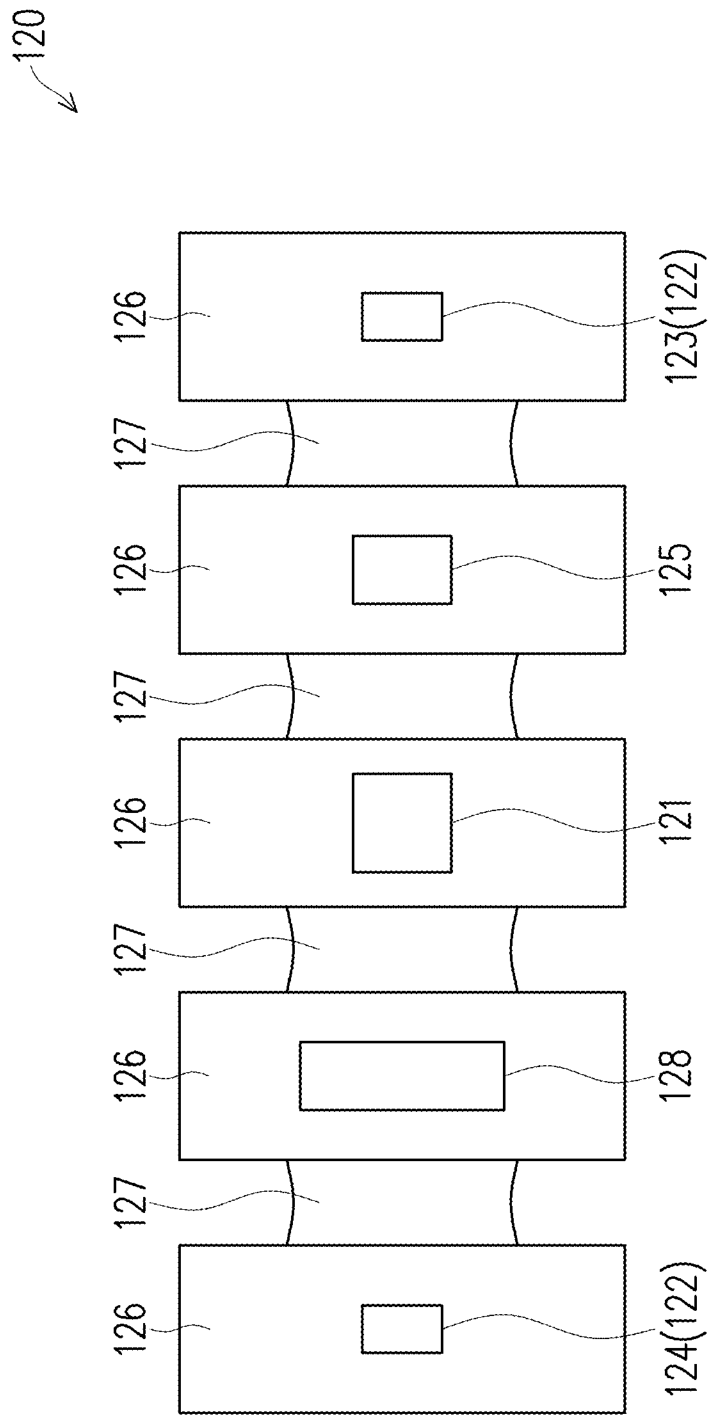
FIG. 2B is a schematic view of the flexible electronic assembly of FIG. 2A being flattened.

FIG. 2A is a schematic view of a flexible electronic assembly of the single-arm physiological signal measuring system of FIG. 1A. FIG. 2B is a schematic view of the flexible electronic assembly of FIG. 2A being flattened. Please refer to FIG. 2A and FIG. 2B. In the embodiment, the flexible electronic assembly 120 is bent along the shape of the shell 110 and is also presented in a C-shape.

As shown in FIG. 2B, the flexible electronic assembly 120 includes a photoplethysmography (PPG) module 121, an electrocardiogram (ECG) module 122, and a controller 125. The photoplethysmography module 121 is configured to measure a blood oxygen saturation of a user, and the electrocardiogram module 122 is configured to measure an electrocardiogram of the user. The photoplethysmography module 121 includes, for example, a light transmitter and a light receiver, and the electrocardiogram module 122 includes a first electrocardiogram electrode 123 and a second electrocardiogram electrode 124.

The photoplethysmography module 121 includes, for example, a photodiode and two light-emitting diodes (LEDs), wherein the light-emitting diode may be a green light-emitting diode or a red light-emitting diode and is configured to emit light into human tissues, and the photodiode is configured to absorb light reflected by human tissues and convert the light into an electrical signal, that is, a PPG signal, to express changes in blood volume in human tissues.

The controller 125 is electrically connected to the photoplethysmography module 121 and the electrocardiogram module 122. In the embodiment, the flexible electronic assembly 120 further includes a cell 128 electrically connected to the controller 125, the photoplethysmography module 121, and the electrocardiogram.

In the embodiment, the flexible electronic assembly includes at least two hard circuit boards 126 and at least one flexible circuit board or at least one flexible cable 127 connecting the at least two hard circuit boards 126. The photoplethysmography module 121, the controller 125, the first electrocardiogram electrode 123, and the second electrocardiogram electrode 124 are respectively disposed on the at least two hard circuit boards 126. The first electrocardiogram electrode 123 and the second electrocardiogram electrode 124 are disposed on two different ones of the at least two hard circuit boards 126 to be separated by a greater distance, so as to increase a detected signal vector difference.

Specifically, the flexible electronic assembly includes five hard circuit boards 126 and four flexible cables 127 connecting the five hard circuit boards 126. The photoplethysmography module 121, the controller 125, the cell 128, the first electrocardiogram electrode 123, and the second electrocardiogram electrode 124 are respectively disposed on the five hard circuit boards 126. The hard circuit boards 126 are electrically connected to each other through the flexible cables 127.

Of course, the number of the hard circuit boards 126 and the flexible cables 127 is not limited thereto. Several of the photoplethysmography module 121, the controller 125, the cell 128, the first electrocardiogram electrode 123, and the second electrocardiogram electrode 124 may also be disposed on the same hard circuit board 126, and the positions where the elements are disposed are not limited thereto. In addition, the hard circuit board 126 can provide optimal structural support for the elements.

Of course, in other embodiments, the flexible electronic assembly 120 may not include the hard circuit board 126, and the photoplethysmography module 121, the controller 125, the cell 128, the first electrocardiogram electrode 123, and the second electrocardiogram electrode 124 may also be disposed on the flexible circuit board (not shown) to correspond to the shape of the shell 110.

Figure 3A:
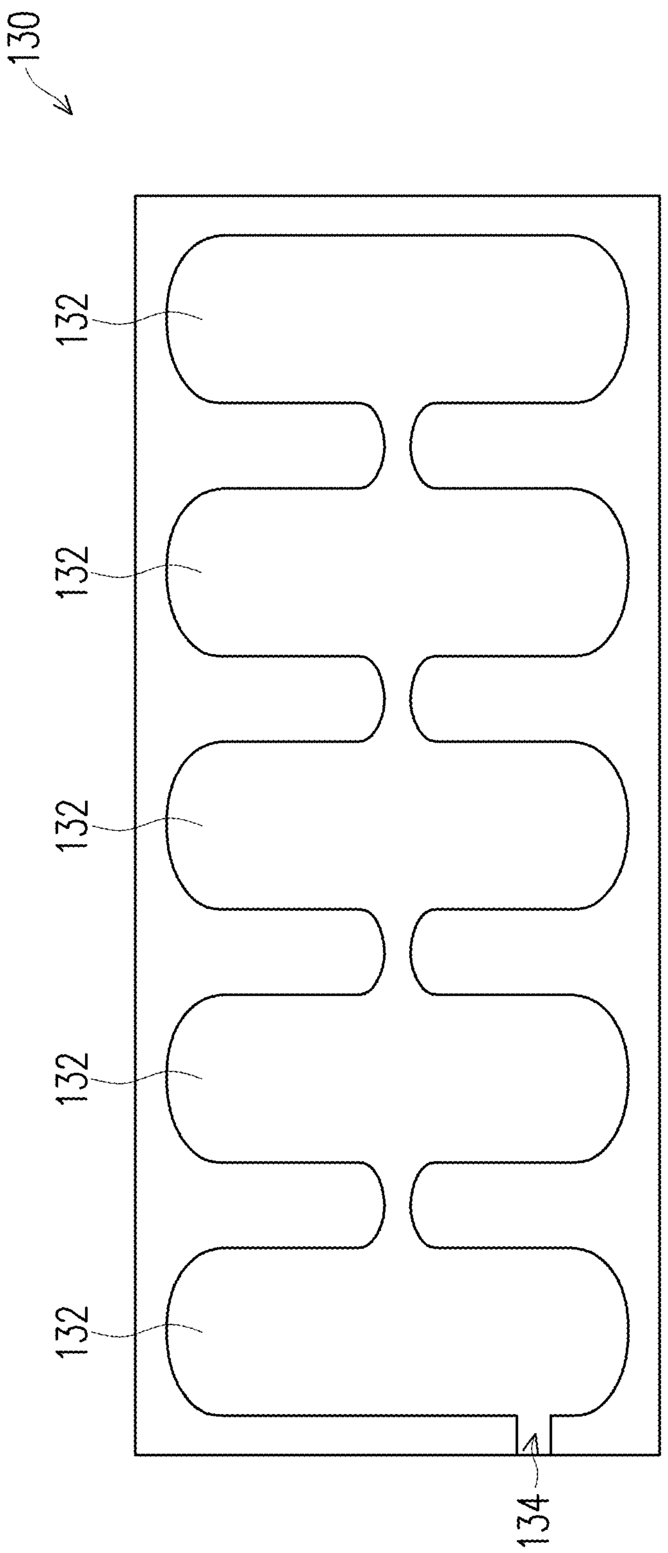
FIG. 3A is a schematic view of an air bag of the single-arm physiological signal measuring system of FIG. 1A being flattened.

FIG. 3A is a schematic view of an air bag of the single-arm physiological signal measuring system of FIG. 1A being flattened. Please refer to FIG. 3A. In the embodiment, the air bag 130 includes multiple pouches 132 evenly arranged and communicated with each other, and an air bag port 134 is communicated with the inflating port 112 (FIG. 1A) of the shell 110 and the pouches 132. Therefore, air may enter the pouch 132 through the inflating port 112 of the shell 110 and the air bag port 134.

In the embodiment, the positions of the pouches 132 correspond to the positions of the hard circuit boards 126 (FIG. 2B). Such design enables the pouches 132 to directly push the corresponding hard circuit boards 126 when inflated, so that elements on the hard circuit boards 126 move. In particular, the photoplethysmography module 121, the first electrocardiogram electrode 123, and the second electrocardiogram electrode 124 can move toward a direction away from the shell 110 to contact the skin of the user.

Of course, in other embodiments, the positions of the pouches 132 may also only correspond to the positions of a part of the hard circuit boards 126, as long as projections of the pouches 132 of the air bag 130 to the flexible electronic assembly 120 cover the photoplethysmography module 121, the first electrocardiogram electrode 123, and the second electrocardiogram electrode 124.

Figure 3B:
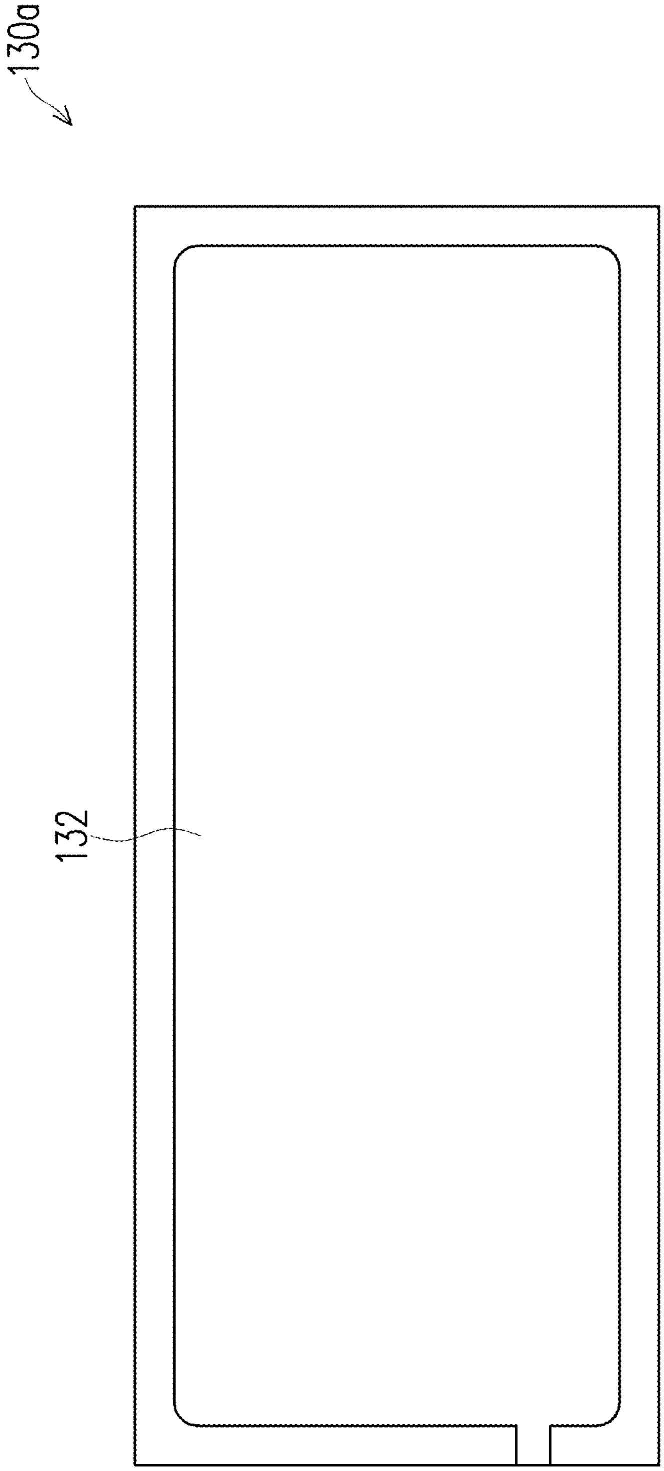
FIG. 3B is a schematic view of an air bag of a single-arm physiological signal measuring system being flattened according to another embodiment of the disclosure.

FIG. 3B is a schematic view of an air bag of a single-arm physiological signal measuring system being flattened according to another embodiment of the disclosure. Please refer to FIG. 3B. The main difference between an air bag 130*a* of FIG. 3B and the air bag 130 of FIG. 3A is that in the embodiment, the air bag 130*a* includes a single pouch 132, and the pouch 132 corresponds to the hard circuit boards 126 (FIG. 2B). Similarly, when the pouch 132 of the air bag 130*a* is inflated, pushing the photoplethysmography module 121, the first electrocardiogram electrode 123, and the second electrocardiogram electrode 124 to contact of the skin of the user can still be achieved.

Figure 4:
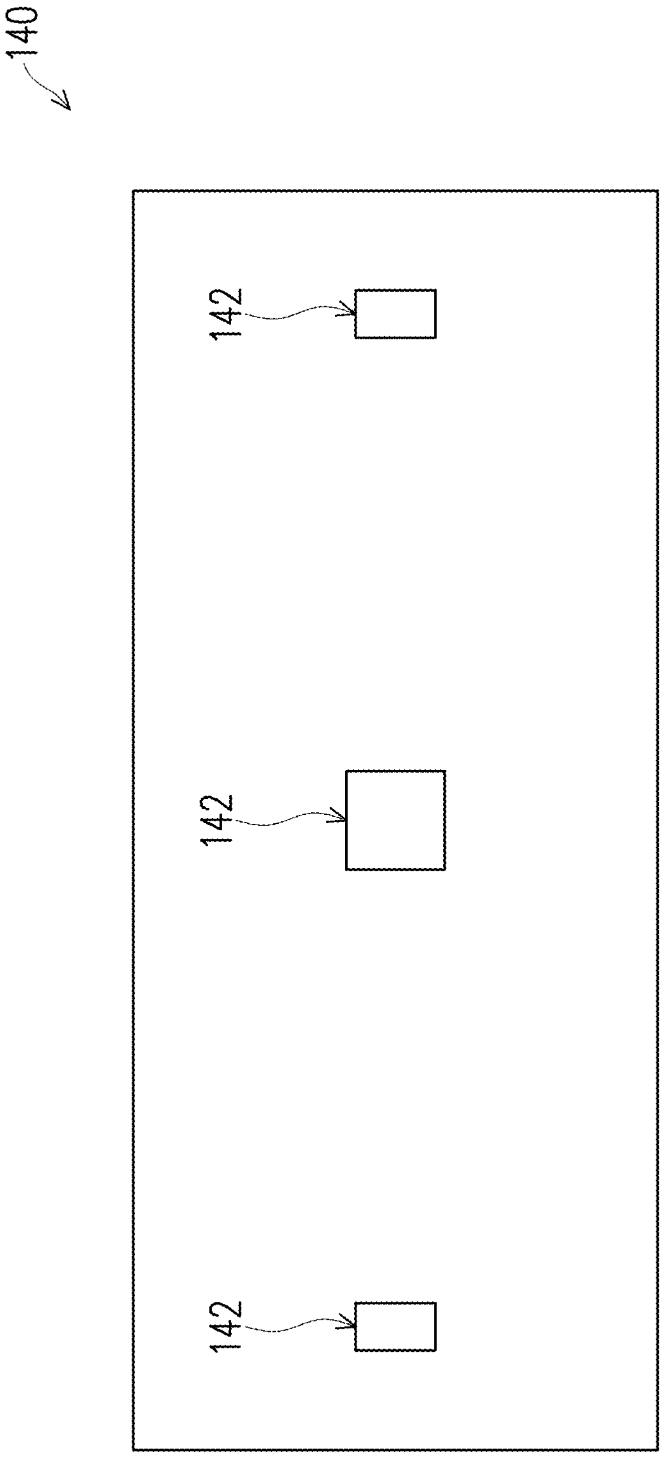
FIG. 4 is a schematic view of a soft layer of the single-arm physiological signal measuring system of FIG. 1A being flattened.

FIG. 4 is a schematic view of a soft layer of the single-arm physiological signal measuring system of FIG. 1A being flattened. Please refer to FIG. 1B and FIG. 4. The single-arm physiological signal measuring system 100 further includes a soft layer 140 disposed on a surface of the flexible electronic assembly 120 facing the space S to cover the flexible electronic assembly 120. Therefore, the soft layer 140 covers the hard circuit board 126 (FIG. 2B), the flexible cable 127 (FIG. 2B), the photoplethysmography module 121 (FIG. 2B), the controller 125 (FIG. 2B), the cell 128 (FIG. 2B), the first electrocardiogram electrode 123 (FIG. 2B), and the second electrocardiogram electrode 124 (FIG. 2B). When the single-arm physiological signal measuring system 100 performs measurement, the skin of the user mainly contacts the soft layer 140, which can effectively improve of the comfort of the user.

Please refer to FIG. 2B and FIG. 4 at the same time. It can be seen that the soft layer 140 includes multiple openings 142, and the openings 142 expose the photoplethysmography module 121, the first electrocardiogram electrode 123, and the second electrocardiogram electrode 124. Therefore, the photoplethysmography module 121, the first electrocardiogram electrode 123, and the second electrocardiogram electrode 124 may directly contact the skin of the user.

Figure 5:
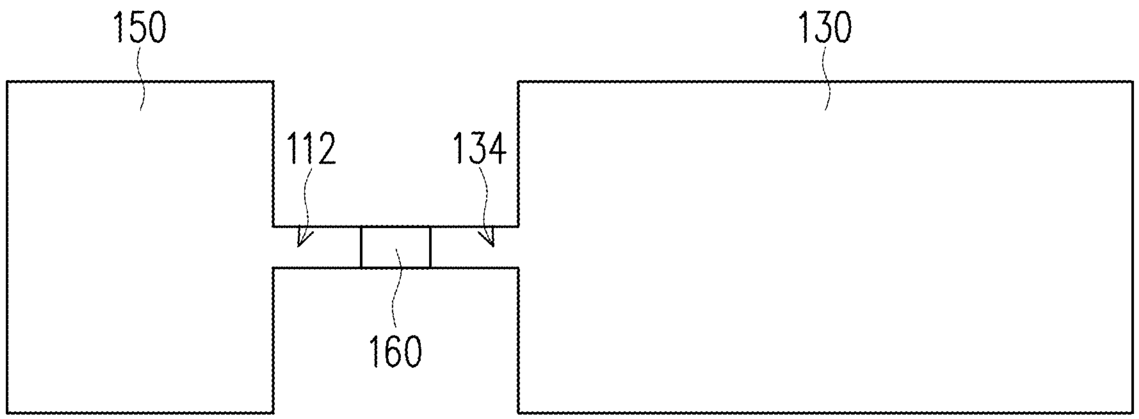
FIG. 5 is a schematic view of an inflating system, a one-way valve, and an air bag of the single-arm physiological signal measuring system of FIG. 1A.

FIG. 5 is a schematic view of an inflating system, a one-way valve, and an air bag of the single-arm physiological signal measuring system of FIG. 1A. Please refer to FIG. 5. In the embodiment, the single-arm physiological signal measuring system 100 may optionally include an inflating system 150. The inflating system 150 may be an electric or manual inflating system. The inflating system 150 is detachably combined with the inflating port 112. Alternatively, in an embodiment, the inflating system 150 may be fixed to the inflating port 112, that is, combined with the shell 110, to prevent the trouble of not finding the inflating system 150 during use.

The inflating system 150 may be communicated with the inflating port 112, and a one-way valve 160 is disposed between the inflating port 112 and the air bag 130 to ensure the flow direction of the air, so that the air may smoothly enter the air bag 130 from the air bag port 134. In addition, the air bag 130 is communicated with the deflating port 114 (FIG. 1A). When the air bag 130 is to be deflated, a plug (not shown) on the deflating port 114 may be opened to deflate the air bag 130.

In the embodiment, an arm of the user is adapted to extend into the space S (FIG. 1A) of the single-arm physiological signal measuring system 100. When the air bag 130 is inflated, the photoplethysmography module 121, the first electrocardiogram electrode 123, and the second electrocardiogram electrode 124 are pushed by the air bag 130 to contact the arm, so that the photoplethysmography module 121 measures the blood oxygen saturation of the user, the electrocardiogram module 122 measures the electrocardiogram of the user, and the controller 125 calculates the blood pressure of the user according to the blood oxygen saturation and the electrocardiogram.

The controller 125 may process and calculate blood pressure estimation by a constructed calculation model. For example, characteristic parameters are calculated for an ECG signal and the PPG signal. The characteristic parameters may include heart rate (HR), pulse arrival time (PAT), pulse-pulse interval (PPI), and pulse width (PW). One set of values of PAT, HR, PPI, and PW may be calculated from waveforms of the ECG signal and the PPG signal between every two heartbeats. Therefore, multiple characteristic parameter data may be obtained by detecting the ECG signal or the PPG signal for a period of time. Next, a reference blood pressure value (including systolic blood pressure and diastolic blood pressure) of the user is input. The reference blood pressure value may be measured by the user using a home blood pressure monitor or a normal blood pressure value input by the user. Then, the reference blood pressure value and the characteristic parameter data are substituted into the calculation model, and a value of a correction coefficient of each characteristic parameter is solved by linear regression. The set of coefficients is obtained according to the ECG signal, the PPG signal, and the reference blood pressure value of the subject, so the set of coefficients includes physiological signal characteristics related to the subject. Then, the ECG signal or the PPG signal is continuously detected, and the waveforms are analyzed in the same manner to obtain the values of PAT, HR, PPI, and PW at this time. Then, the set of correction coefficients is substituted into the calculation model to calculate the blood pressure of the subject.

In other words, the single-arm physiological signal measuring system 100 continuously analyzes and calculates the waveform characteristics of the EEG signal and PPG signal by obtaining continuous ECG signals and PPG signals, thereby continuously estimating the blood pressure values of the subject.

Compared with the conventional manner of measuring blood pressure by obtaining blood pressure information through strapping the air bag 130 to the arm and inflating the air bag 130 to compress the arm, which causes discomfort to the user and can only measure for a short period of time, the air bag 130 of the single-arm physiological signal measuring system 100 of the embodiment only needs to be inflated until the photoplethysmography module 121, the first electrocardiogram electrode 123, and the second electrocardiogram electrode 124 contact the arm to obtain the blood oxygen saturation and the electrocardiogram, and the controller 125 then calculates the blood pressure, which greatly improves the comfort of the user during the measurement process and can achieve long-term measurement.

In other words, the user may wear the single-arm physiological signal measuring system 100 for a long time to obtain long-term physiological signal measurement results, so as obtain more accurate physiological signal information, which can effectively prevent temporary stress during measurement from affecting the measured physiological signal information.

In addition, it is conventional to obtain the blood oxygen saturation at the fingertip, the electrocardiogram at the chest, the hand, or the foot, and the blood pressure at the arm, so the physiological signals are obtained from multiple parts of the body through multiple systems. Multiple physiological signals such as the blood oxygen saturation, the electrocardiogram, and the blood pressure may be obtained in real time by sleeving the single-arm physiological signal measuring system 100 of the embodiment only on the arm of the user, which is fairly simple and convenient to use.

Furthermore, the single-arm physiological signal measuring system 100 of the embodiment defines the space S through the hard shell 110, and enables the photoplethysmography module 121, the first electrocardiogram electrode 123, and the second electrocardiogram electrode 124 to stably contact the arm through the inflating manner, and the user only needs to extend the arm into the space S. The single-arm physiological signal measuring system 100 of the embodiment does not need a buckle or a strap and can be easily operated with one hand, which is very convenient to use and will not loosen during measurement. Of course, in an embodiment, the single-arm physiological signal measuring system 100 of the embodiment may also be provided with the buckle or the strap, which is not limited to the drawings.

In summary, in the single-arm physiological signal measuring system of the disclosure, the air bag is disposed between the shell and the flexible electronic assembly to push the flexible electronic assembly to change the size of the space. The arm of the user is adapted to extend into the space surrounded by the flexible electronic assembly. When the air bag is inflated, the photoplethysmography module, the first electrocardiogram electrode, and the second electrocardiogram electrode of the flexible electronic assembly are pushed by the air bag to contact the arm, so that the photoplethysmography module measures the blood oxygen saturation of the user, the electrocardiogram module of the flexible electronic assembly measures the electrocardiogram of the user, and the controller calculates the blood pressure of the user according to the blood oxygen saturation and the electrocardiogram. Compared with the conventional manner of measuring blood pressure by obtaining blood pressure information through strapping the air bag to the arm and inflating the air bag to compress the arm, which causes discomfort to the user and can only measure for a short period of time, the air bag of the single-arm physiological signal measuring system of the embodiment only needs to be inflated until the photoplethysmography module, the first electrocardiogram electrode, and the second electrocardiogram electrode contact the arm to obtain the blood oxygen saturation and the electrocardiogram, and the controller then calculates the blood pressure, which greatly improves the comfort of the user during the measurement process and can achieve long-term measurement.

What is claimed is:

1. A single-arm physiological signal measuring system, comprising:

a shell;

a flexible electronic assembly, disposed beside an inner surface of the shell, wherein the flexible electronic assembly defines a space configured to receive an arm of a user, the flexible electronic assembly comprising:

a photoplethysmography (PPG) module, comprising a light transmitter and a light receiver;

an electrocardiogram (ECG) module, comprising a first electrocardiogram electrode and a second electrocardiogram electrode;

a controller, electrically connected to the photoplethysmography module and the electrocardiogram module; and an air bag, disposed between the shell and the flexible electronic assembly and configured to push the flexible electronic assembly to change a size of the space, wherein, when the air bag is inflated, the photoplethysmography module, the first electrocardiogram electrode, and the second electrocardiogram electrode are pushed by the air bag in contact with the the arm of the user in the space, wherein the flexible electronic assembly comprises at least two circuit boards, and the first electrocardiogram electrode and the second electrocardiogram electrode are disposed on two different ones of the at least two circuit boards.

2. The single-arm physiological signal measuring system according to claim 1, wherein the flexible electronic assembly further comprises at least one flexible circuit board or at least one flexible cable electrically connecting the at least two circuit boards, and wherein the photoplethysmography module and the controller disposed on the at least two circuit boards.

3. The single-arm physiological signal measuring system according to claim 2, further comprising an inner layer disposed on a surface of the flexible electronic assembly facing the space and covering the at least two circuit boards and the at least one flexible circuit board or the at least one flexible cable, wherein the inner layer comprises a plurality of openings exposing the photoplethysmography module, the first electrocardiogram electrode, and the second electrocardiogram electrode.

4. The single-arm physiological signal measuring system according to claim 1, wherein the flexible electronic assembly further comprises a cell electrically connected to the controller, the photoplethysmography module, and the electrocardiogram module.

5. The single-arm physiological signal measuring system according to claim 1, wherein the air bag comprises a plurality of pouches evenly arranged and communicated with each other, the flexible electronic assembly comprises a plurality of circuit boards, and the pouches correspond to the circuit boards.

6. The single-arm physiological signal measuring system according to claim 1, wherein the air bag comprises a pouch, the flexible electronic assembly comprises a plurality of circuit boards, and the pouch corresponds to the circuit boards.

7. The single-arm physiological signal measuring system according to claim 1, wherein a projection of the air bag onto the flexible electronic assembly covers the photoplethysmography module, the first electrocardiogram electrode, and the second electrocardiogram electrode.

8. The single-arm physiological signal measuring system according to claim 1, wherein the shell comprises an inflating port and a deflating port, the inflating port and the deflating port are communicated with the air bag, and a one-way valve is disposed between the inflating port and the air bag.

9. The single-arm physiological signal measuring system according to claim 8, further comprising an inflating system, wherein the inflating system is detachably combined with the inflating port or the inflating system is fixed to the inflating port.

10. The single-arm physiological signal measuring system according to claim 1, wherein the shell is in a C-shape or an O-shape.

* * * * *